US 11,284,799 B2

United States Patent
Tsai

(10) Patent No.: US 11,284,799 B2
(45) Date of Patent: Mar. 29, 2022

(54) OPTICAL DETECTION DEVICE FOR PHYSIOLOGICAL CHARACTERISTIC IDENTIFICATION

(71) Applicant: PixArt Imaging Inc., Hsin-Chu (TW)

(72) Inventor: Cheng-Nan Tsai, Hsin-Chu (TW)

(73) Assignee: Pix Art Imaging Inc., Hsin-Chu (TW)

( * ) Notice: Subject to any disclaimer, the term of this patent is extended or adjusted under 35 U.S.C. 154(b) by 274 days.

(21) Appl. No.: 16/202,022

(22) Filed: Nov. 27, 2018

(65) Prior Publication Data

US 2020/0163551 A1 May 28, 2020

(51) Int. Cl.
*A61B 5/00* (2006.01)

(52) U.S. Cl.
CPC .... *A61B 5/0059* (2013.01); *A61B 2560/0252* (2013.01); *A61B 2562/0233* (2013.01); *A61B 2562/0271* (2013.01)

(58) Field of Classification Search
CPC .......... A61B 5/0059; A61B 2562/0233; A61B 2562/0271; A61B 2560/0252; A61B 2562/0242; A61B 5/681; A61B 5/0075; A61B 5/1455; A61B 5/14546; A61B 2562/04; A61B 2562/06; A61B 5/145
See application file for complete search history.

(56) References Cited

U.S. PATENT DOCUMENTS

| 2006/0195028 A1* | 8/2006 | Hannula | A61B 5/6804 600/340 |
| 2017/0067778 A1* | 3/2017 | Sugi | G01S 17/88 |

* cited by examiner

*Primary Examiner* — Eric F Winakur
*Assistant Examiner* — Abid A Mustansir
(74) *Attorney, Agent, or Firm* — Winston Hsu

(57) ABSTRACT

An optical detection device for physiological characteristic identification includes a substrate, a light source and an optical receiver. The light source includes a plurality of first lighting units and a plurality of second lighting units symmetrically arranged on the substrate. The optical receiver is disposed on the substrate and adapted to analyze optical signals emitted by the light source for acquiring a result of the physiological characteristic identification.

7 Claims, 6 Drawing Sheets

OPTICAL DETECTION DEVICE FOR PHYSIOLOGICAL CHARACTERISTIC IDENTIFICATION

BACKGROUND OF THE INVENTION

1. Field of the Invention

The present invention relates to an optical detection device, and more particularly, to an optical detection device for preferred physiological characteristic identification.

2. Description of the Prior Art

A conventional optical detection device utilizes an optical signal having a wavelength about 660 nm, 880 nm or 940 nm to detect physiological characteristics (Oxygenated Hemoglobin, HbO2) of the user. Generally, the user may put a finger on the conventional optical detection device for the physiological characteristic identification; however the conventional optical detection device may be designed as a smart wearable device, such as the smart watch, the smart bracelet and the smart necklace. The wrist and the neck cannot provide sufficient signal intensity of the physiological characteristic identification, that is, a design of an optical detection device capable of increasing optical detecting efficiency is an important issue in the related industry.

SUMMARY OF THE INVENTION

The present invention provides an optical detection device for preferred physiological characteristic identification for solving above drawbacks.

According to the claimed invention, an optical detection device for physiological characteristic identification includes a substrate, a light source and an optical receiver. The light source includes a plurality of first lighting units and a plurality of second lighting units symmetrically arranged on the substrate. The optical receiver is disposed on the substrate and adapted to analyze optical signals emitted by the light source for acquiring a result of the physiological characteristic identification.

According to the claimed invention, an optical detection device for physiological characteristic identification includes a first light source, a second light source, a third light source and an optical receiver. The first light source is adapted to emit a first optical signal. The second light source is adapted to emit a second optical signal. The third light source is adapted to emit a third optical signal. The optical receiver is adapted to receive and analyze the first optical signal, the second optical signal and the third optical signal for acquiring a result of the physiological characteristic identification. The first optical signal, the second optical signal and the third optical signal have wavelengths different from each other.

According to the claimed invention, an optical detection device for physiological characteristic identification includes a light source and an optical receiver. The light source is adapted to emit an optical signal having a wavelength ranged of 600 to 630 nm. The optical receiver is adapted to receive and analyze the optical signal for acquiring a result of the physiological characteristic identification.

The present invention utilizes several ways to improve the result of the physiological characteristic identification. The optical detection device may utilize one optical signal with the wavelength ranged around 600 to 630 nm, or utilize two optical signals emitted by the lighting units arranged in symmetry, or utilize three optical signals having the wavelengths different from each other to detect the physiological characteristics for the preferred detection result.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
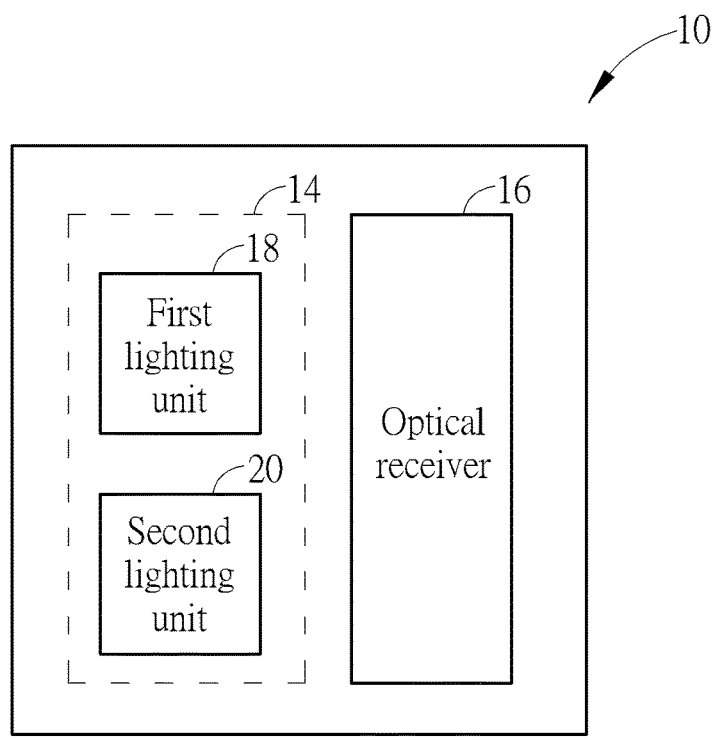
FIG. 1 is a functional block diagram of an optical detection device according to a first embodiment of the present invention.
Figure 2:
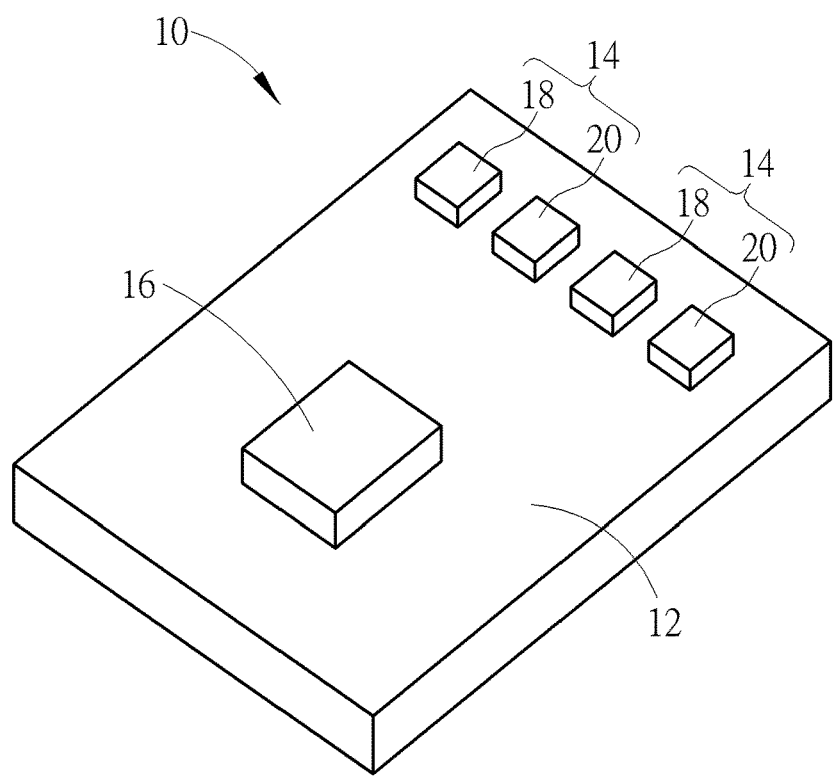
FIG. 2 is a schematic diagram of the optical detection device according to the first embodiment of the present invention.
Figure 3:
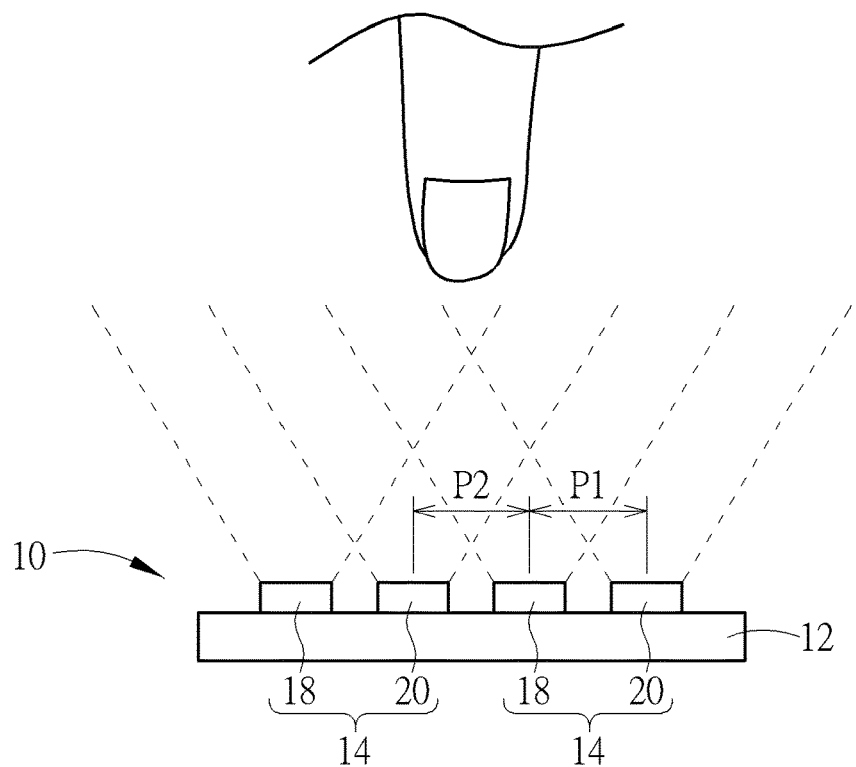
FIG. 3 is another view of the optical detection device shown in FIG. 2.

Please refer to FIG. 1 to FIG. 3. FIG. 1 is a functional block diagram of an optical detection device 10 according to a first embodiment of the present invention. FIG. 2 is a schematic diagram of the optical detection device 10 according to the first embodiment of the present invention. FIG. 3 is another view of the optical detection device 10 shown in FIG. 2. The optical detection device 10 can include a substrate 12, a light source 14 and an optical receiver 16. The light source 14 can utilize at least one first lighting unit 18 and at least one second lighting unit 20 to project optical signals onto the user's skin for physiological characteristic identification. The first lighting unit 18 and the second lighting unit 20 have different wavelengths and preferably are plural, and the plurality of first lighting units 18 and the plurality of second lighting units 20 are symmetrically arranged on the substrate 12. The optical receiver 16 can be disposed on the substrate 12 and adjacent to the light source 14. The optical receiver 16 can analyze the optical signals reflected from the user's skin for acquiring a result of the physiological characteristic identification.

In the first embodiment, the plurality of first lighting units 18 are interlaced with the plurality of second lighting units 20, and a pitch P1 between one first lighting unit 18 and one second lighting unit 20 is the same as a pitch P2 between the foresaid first lighting unit 18 and another second lighting unit 20. Accordingly, the pitch between one second lighting unit 20 and one first lighting unit 18 is the same as the pitch between the foresaid second lighting unit 20 and another first lighting unit 18. The optical signals generated by the first lighting unit 18 and the second lighting unit 20 are divergent beams. As the first lighting unit 18 and the second lighting unit 20 are symmetrically arranged, the optical signals of the first lighting units 18 and the second lighting units 20 projected onto the user's skin are overlapped to establish a region having mixed beams with different wavelengths, so as to eliminate diversity of projection positions between the first lighting unit 18 and the second lighting unit 20, and to acquire the preferred result of the physiological characteristic identification.

An amount and an arrangement of the first lighting unit 18 and the second lighting unit 20 are not limited to the above-mentioned embodiment, and depend on design demand. As shown in FIG. 3, a central region above the optical detection device 10 can gather the beams emitted by the first lighting units 18 and the second lighting units 20 uniformly. The user may put the finger or the wrist or the neck on the central region above the optical detection device 10, and the optical receiver 16 can acquire a preferred reflection pattern for the physiological characteristic identification.

Figure 4:
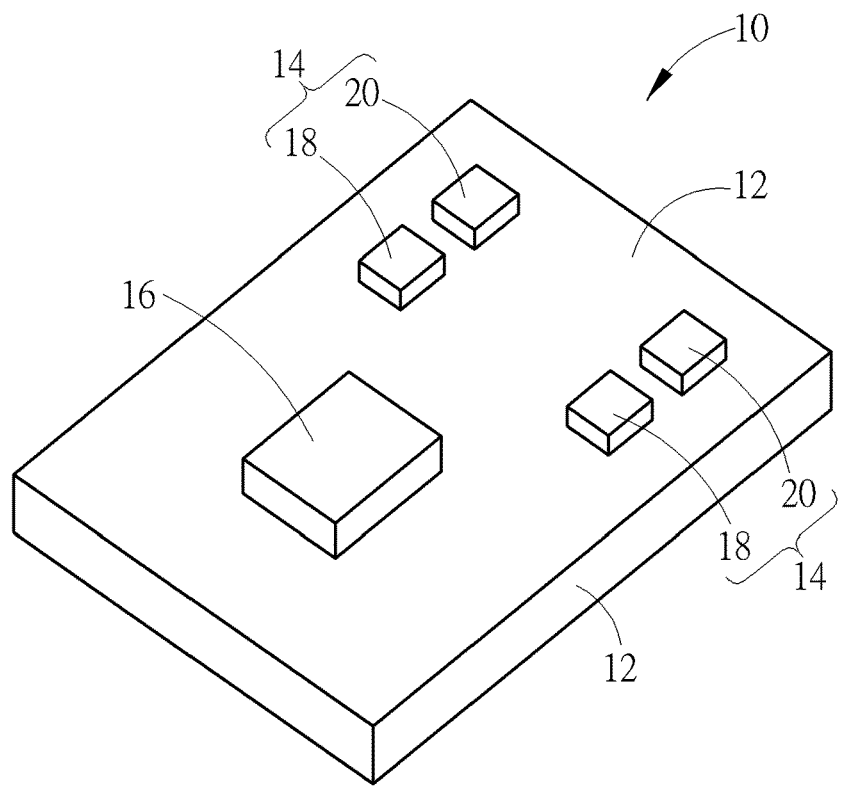
FIG. 4 and FIG. 5 are schematic diagrams of the optical detection device in various applications according to the first embodiment of the present invention.
Figure 5:
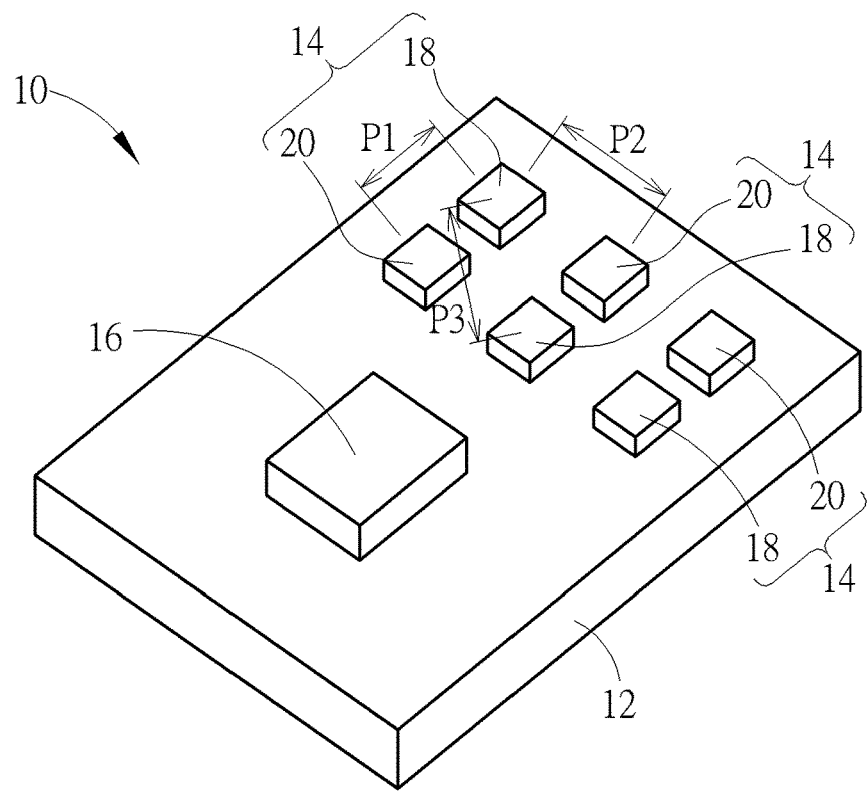

Please refer to FIG. 4 and FIG. 5. FIG. 4 and FIG. 5 are schematic diagrams of the optical detection device 10 in various applications according to the first embodiment of the present invention. As shown in FIG. 4, each light source 14 is consisted of one first lighting unit 18 and one second lighting unit 20, and the optical detection device 10 can dispose a plurality of light sources 14 on a side of the optical receiver 16. A symmetrical arrangement about the first lighting units 18 and the second lighting units 20 can represent an arrangement about one first lighting unit 18 and one second lighting unit 20 (such as the right-side light source 14) is a mirror image of another arrangement about another first lighting unit 18 and another second lighting unit 20 (such as the left-side light source 14). The optical detection device 10 can acquire the preferred result of the physiological characteristic identification if a large number of the light sources 14 is uniformly disposed adjacent to the optical receiver 16; for example, a distance between the optical receiver 16 and a center of the right-side light source 14 is the same as a distance between the optical receiver 16 and a center of the left-side light source 14.

As shown in FIG. 5, each light source 14 is consisted of one first lighting unit 18 and one second lighting unit 20, and a symmetrical arrangement about the first lighting units 18 and the second lighting units 20 can represent an arrangement about one first lighting unit 18 and one second lighting unit 20 (such as the middle light source 14) is able to take the place of another arrangement about another first lighting unit 18 and another second lighting unit 20 (such as the right-side light source 14 or the left-side light source 14) in response to the previously-mentioned arrangement (which means the middle light source 14) turned one hundred and eighty degrees. In addition, the pitch P1 between one first lighting unit 18 and one second lighting unit 20 is the same as the pitch P2 between the foresaid first lighting unit 18 and another second lighting unit 20, and the pitch P1 and the pitch P2 is smaller than a pitch P3 between the foresaid first lighting unit 18 and another first lighting unit 18, which means the plurality of first lighting units 18 and the plurality of second lighting units 20 can be symmetrically arranged as a matrix. Numeral of columns and rows of the matrix is not limited to the embodiment shown in FIG. 5.

Figure 6:
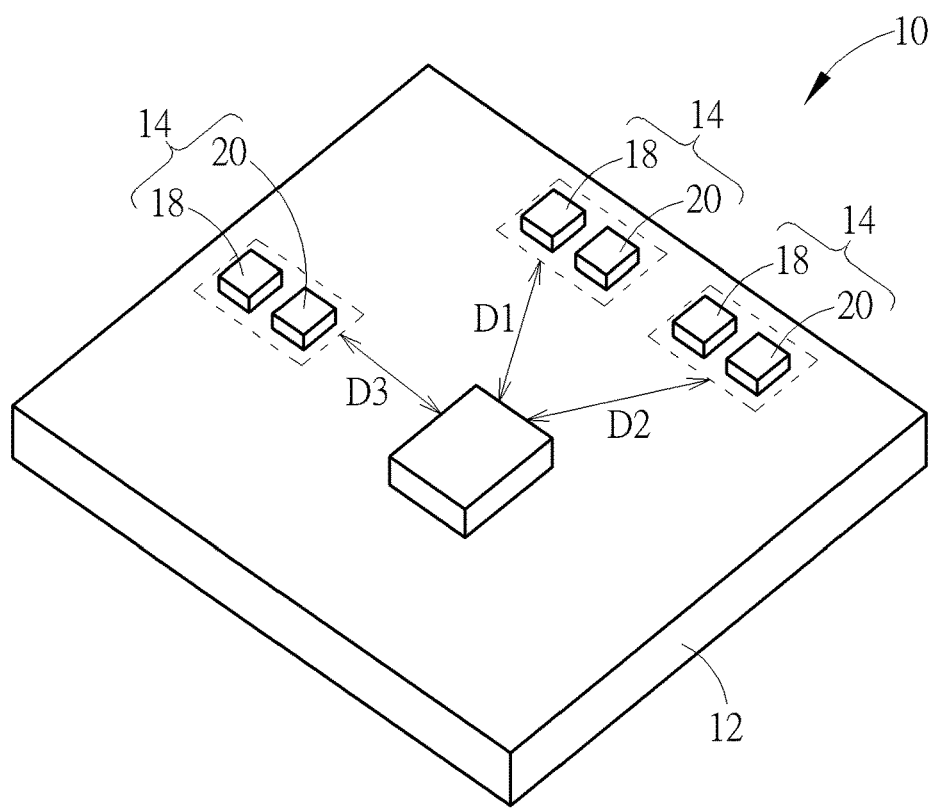
FIG. 6 is a schematic diagram of the optical detection device in another application according to the first embodiment of the present invention.

Please refer to FIG. 6. FIG. 6 is a schematic diagram of the optical detection device 10 in another application according to the first embodiment of the present invention. Several sets (such as the light sources 14 shown in FIG. 6) consisted of one first lighting unit 18 and one second lighting unit 20 are established, and each set has parameters relevant to the optical receiver 16 is similar to another set's parameters relevant to the optical receiver 16. For example, the symmetrical arrangement about the first lighting units 18 and the second lighting units 20 can represent that a distance D1 between the optical receiver 16 and a set of the first lighting unit 18 and the second lighting unit 20 is the same as or similar to another distance D2 and D3 between the optical receiver 16 and a set of another first lighting unit 18 and another second lighting unit 20. The light sources 14 can be disposed around the first lighting units 18 as long as the distances between the optical receiver 16 and each light source 14 are similar even the same.

According to the above-mentioned application of the first embodiment, the plurality of light sources 14 can be disposed adjacent to the same side of the optical receiver 16 or disposed around several sides of the optical receiver 16 for the symmetrical arrangement. Each light source 14 can have one or plural sets consisted of one first lighting unit 18 and one second lighting unit 20, which depends on its structural strength. The distance between the optical receiver 16 and the plural sets containing the first lighting unit 18 and the second lighting unit 20 preferably are the same or similar to each other. Furthermore, a distance between the optical receiver 16 and an arrangement center of the light sources 14 may be preferably ranged of 5 to 15 mm.

Figure 7:
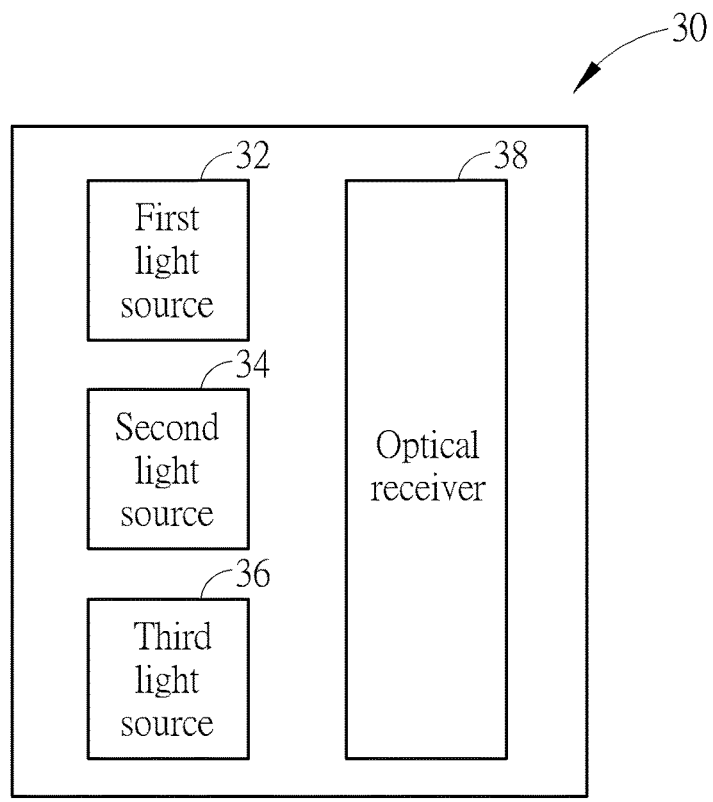
FIG. 7 is a functional block diagram of an optical detection device according to a second embodiment of the present invention.
Figure 8:
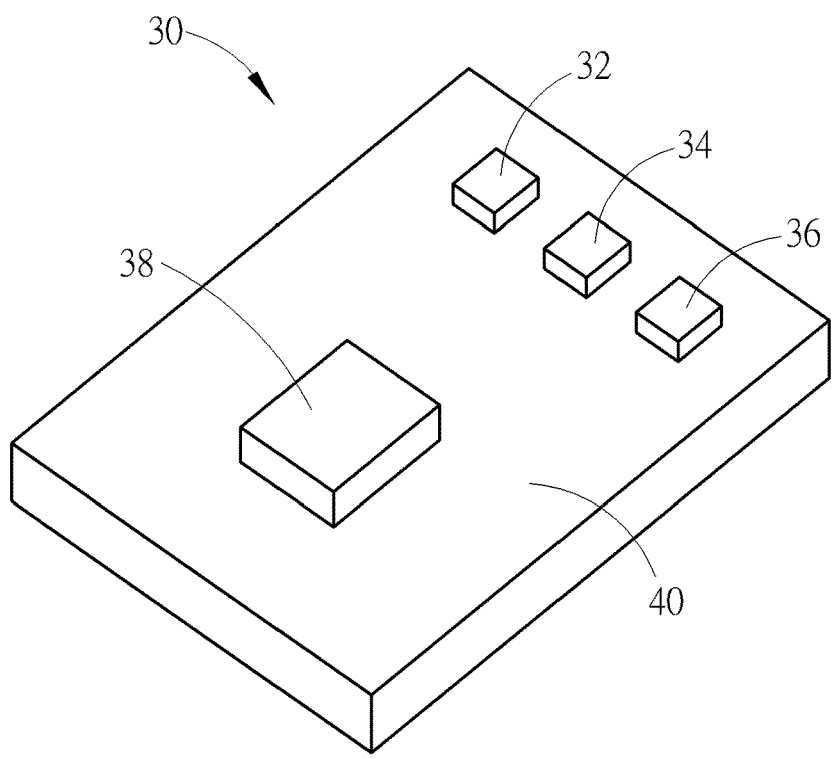
FIG. 8 is a schematic diagram of the optical detection device according to the second embodiment of the present invention.
Figure 9:
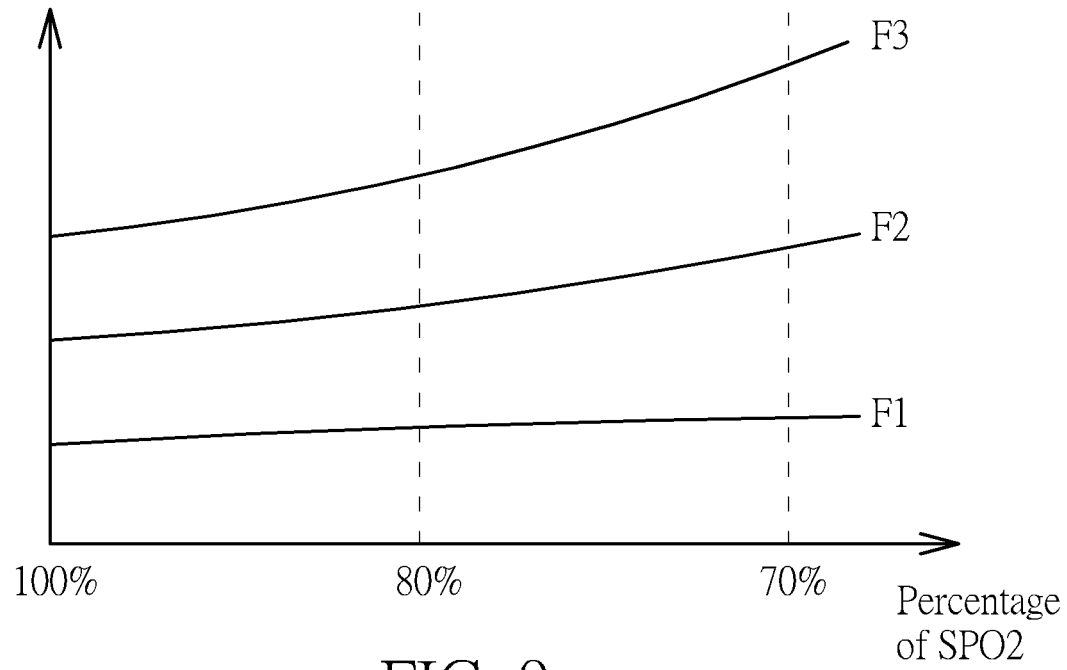
FIG. 9 is a diagram of functional curves between different optical signals according to the second embodiment of the present invention.

Please refer to FIG. 7 to FIG. 9. FIG. 7 is a functional block diagram of an optical detection device 30 according to a second embodiment of the present invention. FIG. 8 is a schematic diagram of the optical detection device 30 according to the second embodiment of the present invention. FIG. 9 is a diagram of functional curves between different optical signals according to the second embodiment of the present invention. The optical detection device 30 can include a first light source 32, a second light source 34, a third light source 36, an optical receiver 38 and a substrate 40. The first light source 32, the second light source 34 and the third light source 36 are disposed on the substrate 40 and adjacent to the optical receiver 38. The first light source 32, the second light source 34 and the third light source 36 are used to respectively emit a first optical signal, a second optical signal and a third optical signal, respectively having wavelengths different from each other. For instance, the wavelength of the first optical signal may be ranged about 660 nm, and the wavelength of the second optical signal may be ranged about 880 nm, and the wavelength of the third optical signal may be in the range of 660 to 880 nm.

The optical receiver 38 may have a built-in processor or receive a processing result from an external component; therefore, the optical receiver 38 can analyze the first optical signal, the second optical signal and the third optical signal reflected from the user's skin to detect physiological characteristics of the user, such as Oxygenated Hemoglobin (HbO2). Relation between the first optical signal and the second optical signal can generate a first function F1; relation between the first optical signal and the third optical signal can generate a second function F2; relation between the second optical signal and the third optical signal can generate a third function F3. The first function F1, the second function F2 and the third function F3 are varied accordingly when the first optical signal, the second optical signal and the third optical signal are projected onto the pressed biological organization, and the optical receiver 38 can receive and analyze the functions F1, F2 and F3 to determine what information is reasonable for following analysis and what information is unreasonable for being removed, so as to acquire the high-precision result of the physiological characteristic identification. The said functions can be a ratio of one of the optical signals to another optical signal, or an equation relevant to two of the optical signals.

Figure 10:
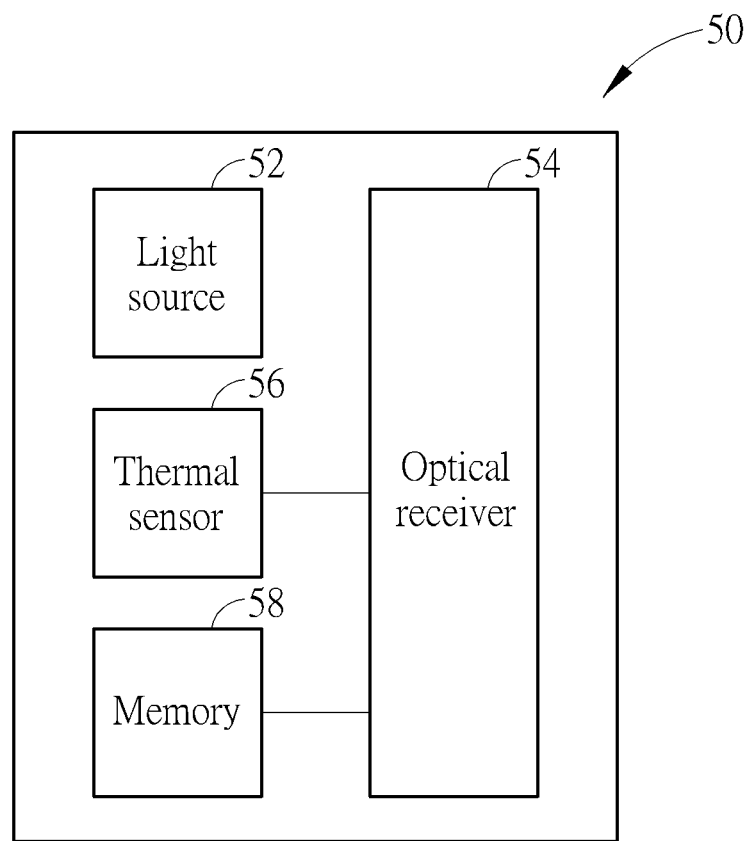
FIG. 10 is a functional block diagram of an optical detection device according to a third embodiment of the present invention.
Figure 11:
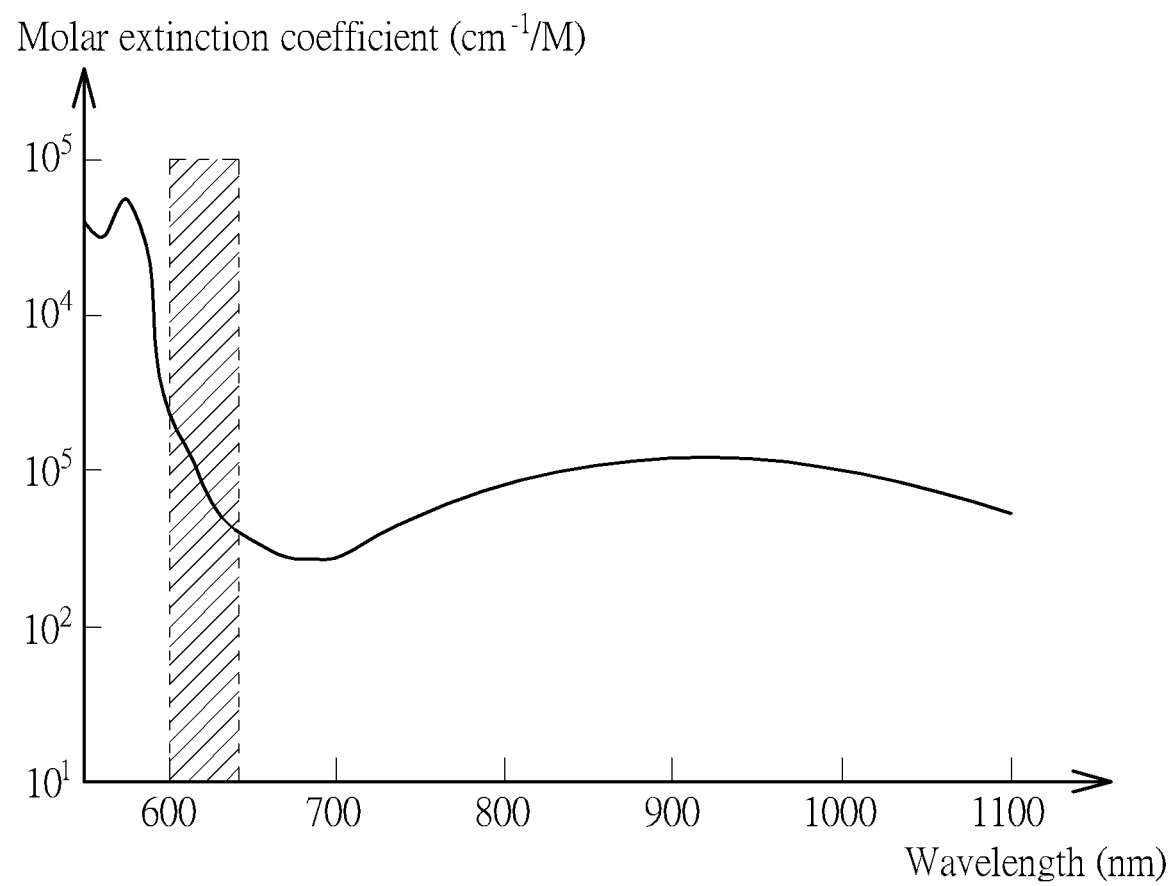
FIG. 11 is a diagram of coefficient variation detected by the optical detection device according to the third embodiment of the present invention.

Please refer to FIG. 10 and FIG. 11. FIG. 10 is a functional block diagram of an optical detection device 50 according to a third embodiment of the present invention. FIG. 11 is a diagram of coefficient variation detected by the optical detection device 50 according to the third embodiment of the present invention. The optical detection device 50 can include a light source 52 and an optical receiver 54. The light source 52 can be utilized to emit an optical signal having a wavelength ranged of 600 to 630 nm. The optical receiver 54 can analyze the foresaid optical signal reflected from the biological organization to acquire the result of the physiological characteristic identification. The conventional optical detection technology utilizes the optical signal with a wavelength ranged about 660 nm but cannot acquire sufficient signal intensity for identification analysis; for this reason, the optical detection device 50 which utilizes the optical signal having the wavelength ranged around 600 to 630 nm can effectively increase the signal intensity, as an area with inclined lines shown in FIG. 11, so as to acquire the preferred result of the physiological characteristic identification.

The optical detection device 50 can further include a thermal sensor 56 and a memory 58 both are electrically connected to the optical receiver 54. The optical detection device 50 can actuate the thermal sensor 56 to sense ambient temperature or temperature of an electronic unit, and compensate the result of the physiological characteristic identification in accordance with a sensing result of the thermal sensor 56 for increasing an accuracy of the physiological characteristic identification. For instance, the electronic unit can be an integrated circuit or any heat generating components nearby the optical detection device 50. The memory 58 can be used to store relation between the sensed temperature and the result of the physiological characteristic identification. As temperature variation is sensed, a compensating parameter of the physiological characteristic identification can be searched from a look-up table about the said relation stored in the memory 58, and the compensating parameter is applied to amend the result of the physiological characteristic identification for overcoming inaccuracy resulted by the optical signal with the wavelength ranged around 600 to 630 nm.

In conclusion, the present invention utilizes several ways to improve the result of the physiological characteristic identification. The optical detection device may utilize one optical signal with the wavelength ranged around 600 to 630 nm, or utilize two optical signals emitted by the lighting units arranged in symmetry, or utilize three optical signals having the wavelengths different from each other to detect the physiological characteristics for the preferred detection result.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical detection device for physiological characteristic identification, comprising:
    a substrate;
    a light source, comprising a plurality of first lighting units and a plurality of second lighting units symmetrically arranged on the substrate, each of the plurality of first lighting units having a wavelength different from a wavelength of each of the plurality of second lighting units, and only one of the plurality of first lighting units being alternately disposed between two adjacent second lighting units, wherein the first lighting unit and the second lighting unit are light emitting diodes; and
    an optical receiver disposed on the substrate and adapted to simultaneously analyze optical signals emitted by the plurality of first lighting units and the plurality of second lighting units for acquiring a result of the physiological characteristic identification.

2. The optical detection device of claim 1, wherein the plurality of first lighting units and the plurality of second lighting units are arranged as a matrix, and the plurality of first lighting units are interlaced with the plurality of second lighting units.

3. The optical detection device of claim 1, wherein a pitch between one of the plurality of first lighting units and any of the second lighting units is the same.

4. The optical detection device of claim 1, wherein a pitch between one of the plurality of first lighting units and any of the second lighting units is smaller than a pitch between the foresaid first lighting unit and another first lighting unit.

5. The optical detection device of claim 1, wherein the symmetrical arrangement about the plurality of first lighting units and the plurality of second lighting units represents an arrangement about one of the plurality of first lighting units and one of the plurality of second lighting units is turned one hundred and eighty degrees to be identical with an arrangement about another first lighting unit and another second lighting unit.

6. The optical detection device of claim 1, wherein the symmetrical arrangement about the plurality of first lighting units and the plurality of second lighting units represents a distance between the optical receiver and a set of a first lighting unit and a second lighting unit is the same as a distance between the optical receiver and a set of another first lighting unit and another second lighting unit.

7. The optical detection device of claim 1, wherein a distance between the optical receiver and a center of the light source is ranged of 5 to 15 mm.

* * * * *